United States Patent

Koch et al.

[11] Patent Number: 5,767,292
[45] Date of Patent: Jun. 16, 1998

[54] PROCESSES FOR PREPARING 1-METHOXY-2-PROPYL 3-(7-DIETHYLAMINO-2-OXO-2H-CHROMEN-3-YL)-3-OXOPROPIONATE

[75] Inventors: Peter Koch, Obertshausen; Wolfgang Bauer, Maintal, both of Germany

[73] Assignee: Hoechst Aktiengesellschaft, Frankfurt, Germany

[21] Appl. No.: 861,964

[22] Filed: May 22, 1997

[30] Foreign Application Priority Data

May 23, 1996 [DE] Germany .......... 196 20 747.9

[51] Int. Cl.[6] .......... C07D 311/02; C07C 69/66
[52] U.S. Cl. .......... 549/287; 560/176
[58] Field of Search .......... 549/287; 560/176

[56] References Cited

U.S. PATENT DOCUMENTS 4,147,552  4/1979  Specht et al. .......... 96/115
5,225,312  7/1993  Dixit et al. .......... 430/191

FOREIGN PATENT DOCUMENTS 2704368  2/1976  Germany .

OTHER PUBLICATIONS

Advanced Organic Chemistry, Reactions, Mechanisms, and Structure: Fourth Edition, Jerry March : US, New–York, Wiley & Sons, (1992) p. 397.

*Primary Examiner*—Bernard Dentz
*Attorney, Agent, or Firm*—Scott E. Hanf

[57] ABSTRACT

The present invention relates to processes for preparing 1-methoxy-2-propyl 3-(7-diethylamino-2-oxo-2H-chromen-3-yl)-3-oxopropionate of the formula I and also di(1-methoxy-2-propyl) acetonedicarboxylate as intermediate for one of the processes.

16 Claims, No Drawings

PROCESSES FOR PREPARING 1-METHOXY-2-PROPYL 3-(7-DIETHYLAMINO-2-OXO-2H-CHROMEN-3-YL)-3-OXOPROPIONATE

The present invention relates to processes for preparing 1-methoxy-2-propyl 3-(7-diethylamino-2-oxo-2H-chromen-3-yl)-3-oxopropionate of the formula I

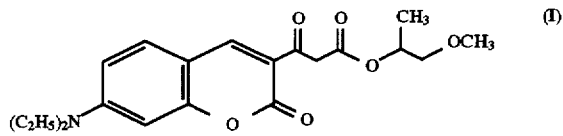

and also di(1-methoxy-2-propyl) acetonedicarboxylate as new intermediate for one of the processes.

The methoxypropyl ester of the formula I is used as a dye for photoresists, in particular photoresists based on novolak resins and quinonediazides. Compared with the corresponding methyl ester, which is likewise used as a dye for photoresists, the methoxypropyl ester of the formula I has more favorable solubility properties. Further details on the ester of the formula I and its use are given in the patent U.S. Pat. No. 5,225,312, the full contents of which are hereby incorporated by reference into the present disclosure.

U.S. Pat. No. 5,225,312 describes a process for preparing I in which the corresponding methyl ester of the formula II, which according to DE-C-2 704 368 is obtainable from 4-diethylaminosalicylaldehyde and dimethyl acetonedicarboxylate with base catalysis, is transesterified with 1-methoxy-2-propanol of the formula III in the presence of sulfuric acid as catalyst with methanol being distilled off.

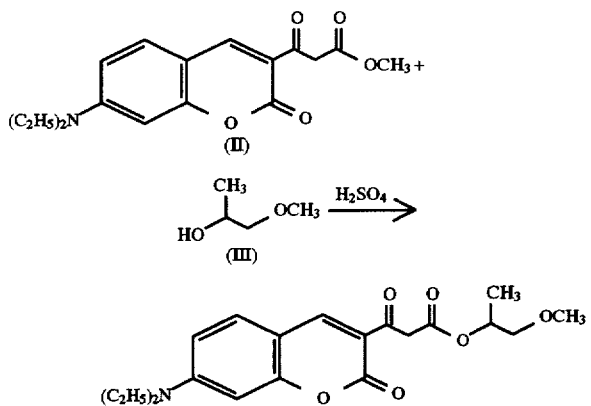

However, the product of this transesterification, which is isolated after neutralization of the sulfuric acid with morpholine by precipitation with water, filtration and washing, still comprises predominantly unreacted methyl ester of the formula II. According to U.S. Pat. No. 5,225,312, such a product is, however, suitable for use in photoresists and is used for this purpose. Owing to its better solubility, for example in ethyl lactate, it has advantages compared with the pure methyl ester of the formula II.

The process known from U.S. Pat. No. 5,225,312 for preparing I or for preparing a mixture of I and II nevertheless has a series of disadvantages. Thus, large excesses of transesterification alcohol and catalyst are required, viz. 26.4 mol of III per mol of II and 1.27 mol of sulfuric acid per mol of II. Owing to the large amount of 1-methoxy-2-propanol and the good solubility of the resulting product in this solvent, a large volume of water is required for precipitation, which has as a consequence a poor space yield of about 26 l per kg of transesterification product. The aqueous work-up results in wastewater containing 1-methoxy-2-propanol, morpholine and further organic constituents which has to be treated or disposed of.

According to U.S. Pat. No. 5,225,312, the yield of transesterification product is only 86.7 percent by weight, based on the weight of the methyl ester of the formula II used, and the product contains not only the esters I and II but also numerous impurities, as is shown when it is analyzed by high-pressure liquid chromatography (HPLC). In addition, the achievable degree of transesterification is very low. HPLC indicates that the product comprises about 2.7 parts of compound II per 1 part of compound I: unreacted starting material therefore predominates by far.

It is therefore an object of the present invention to provide new processes for preparing the methoxypropyl ester of the formula I which avoid the disadvantages of the known process.

It has surprisingly been found that this object is achieved when the transesterification of the methyl ester of the formula II with the alcohol III described in U.S. Pat. No. 5,225,312 is carried out without addition of a catalyst. Transesterification reactions generally require acid or base catalysis, see, for example, J. March, Advanced Organic Chemistry, 3rd edition, page 351, Wiley, New York 1985. Transesterifications under neutral conditions have been described only rarely and usually require specific auxiliaries, e.g. phosphorus ylides (see Tetrahedron Lett. 21 (1980), 2857), the adduct of diethyl azodicarboxylate and triphenylphosphine (see Tetrahedron Lett. 1975, 3871) or iodotrimethylsilane (see Synthesis 1981, 142). Certain specific esters can be transesterified under neutral conditions without addition of an auxiliary, but the reaction rates are usually low. Thus, for example, enolizable esters such as acetoacetic esters can be transesterified under neutral conditions, although for these substrates the conditions can be regarded not as neutral but as acid owing to the acid hydrogen atoms in enolizable compounds; however, the mechanism by which such transesterifications proceed is not certain (see J. Am. Chem. Soc. 73 (1951), 4195 and 74 (1952), 3992). α,α-Disubstituted acetoacetic esters which are not enolizable cannot be transesterified in this way (J. Chem. Soc. 89 (1906), 381). The transesterification of esters of strong organic acids, e.g. of oxalic esters or fumaric esters, which occurs under neutral conditions is explained by inductive effects (see J. Am. Chem. Soc. 74 (1952), 3992).

On the basis of this prior art, it was not to be expected that the propionic ester of the formula II would be able to be transesterified with 1-methoxy-2-propanol under neutral conditions. Comparable inductive effects as in the case of oxalic esters or fumaric esters are not present in the case of II. Likewise, acid catalysis effected by the hydrogen atoms of the enolizable β-ketoester function cannot be responsible for the effect observed since the diethylamino group in the molecule of the formula II represents a basic center by means of which the enol protons are neutralized. On the other hand, however, the diethylamino group cannot catalyze the transesterification as a base since an efficient base catalysis requires strong bases which can convert the 1-methoxy-2-propanol into its anion. The basicity of the amino group is not sufficient for this purpose. The observed transesterification without addition of a catalyst is thus highly surprising.

The present invention accordingly provides a process for preparing 1-methoxy-2-propyl 3-(7-diethylamino-2-oxo-2H-chromen-3-yl)-3-oxopropionate of the formula I or mixtures of 1-methoxy-2-propyl 3-(7-diethylamino-2-oxo-2H-chromen-3-yl)-3-oxopropionate of the formula I and methyl 3-(7-diethylamino-2-oxo-2H-chromen-3-yl)-3-oxopropionate of the formula II by transesterification of methyl 3-(7-diethylamino-2-oxo-2H-chromen-3-yl)-3-oxopropionate of the formula II with 1-methoxy-2-propanol of the formula III,

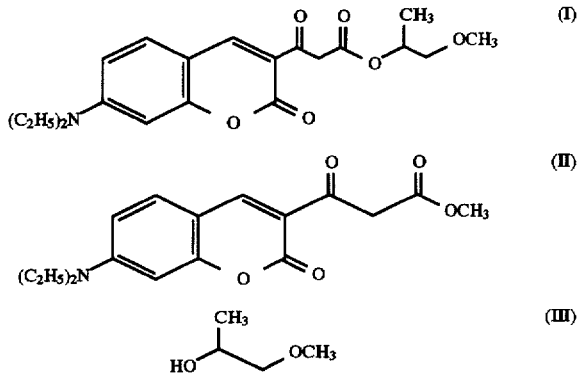

wherein no catalyst is added in the transesterification.

The transesterification is carried out in the customary manner at elevated temperatures. It can be carried out in the presence of an additional inert solvent or diluent, but it is preferably carried out without addition of such a solvent or diluent. The methyl ester of the formula II and the 1-methoxy-2-propanol of the formula III are generally mixed in the desired ratio, the mixture is heated while stirring to the desired reaction temperature and is held at this temperature until the reaction is complete or the desired degree of conversion has been reached. However, for example, the 1-methoxy-2-propanol can also be initially charged at elevated temperature and the methyl ester of the formula II can be added to the hot alcohol. The methanol formed in the reaction can remain in the reaction mixture or be distilled off during the transesterification. It is preferably not distilled off. The reaction is preferably carried out at from 80° to 150° C., particularly preferably at from 90° to 130° C., very particularly preferably at from 100° to 120° C. It can be carried out at atmospheric pressure or under superatmospheric pressure, in particular at a pressure between atmospheric pressure and 6 bar, but it can likewise, particularly when the methanol formed is to be distilled off, be carried out under subatmospheric pressure, i.e. with application of vacuum. The transesterification is preferably carried out at atmospheric pressure. The reaction generally takes from 1 to 4 hours. The end point of the reaction or the achievement of the desired degree of conversion can be determined, for example, by chromatographic analysis of the reaction mixture.

The ratio of methyl ester of the formula II to 1-methoxy-2-propanol of the formula III in the reaction depends, inter alia, on the desired degree of conversion. For the application in photoresists, it is common to use, as described in U.S. Pat. No. 5,225,312, not a pure 1-methoxy-2-propyl ester of the formula I but a mixture of this and the methyl ester of the formula II. When the transesterification process of the invention is employed, degrees of conversion which are comparable to or higher than those obtained by the process of U.S. Pat. No. 5,225,312 can be achieved using significantly lower excesses of 1-methoxy-2-propanol. The transesterification is preferably carried out using from 5 to 10 mol, particularly preferably from 6 to 8 mol, of 1-methoxy-2-propanol of the formula III per mol of methyl ester of the formula II. The 1-methoxy-2-propanol can be used as the racemate, in the form of the pure enantiomers or as a mixture of the enantiomers in any ratio.

The advantage of the process of the invention, namely that only a relatively small excess of 1-methoxy-2-propanol is required for the transesterification, also makes possible an improved work-up compared with the prior art. The transesterification product, i.e. the 1-methoxy-2-propyl ester of the formula I or the mixture of this and of the methyl ester of the formula II, can be isolated from the reaction mixture as described in U.S. Pat. No. 5,225,312 by precipitation with water and filtering off the precipitated product. Owing to the smaller excess of 1-methoxy-2-propanol, the amount of water can also be reduced. However, the reaction mixture from the transesterification is preferably subjected to a nonaqueous work-up. Thus, it can be cooled in a simple manner after the transesterification reaction is complete, preferably to a temperature of from 0° to 20° C., particularly preferably to a temperature of from 3° to 5° C., and the product which has crystallized out can then be isolated by filtration or centrifugation. If desired, it is also possible for part of the 1-methoxy-2-propanol or the mixture of 1-methoxy-2-propanol and methanol to be distilled off before cooling, e.g. by partial evaporation under reduced pressure. In a particularly preferred work-up method, the reaction mixture is, if desired after partial evaporation, admixed with an organic solvent in which the product is sparingly soluble. The addition of the organic solvent can be carried out while the reaction mixture is still hot in order to improve the crystallization of the product. Very particularly preferably, the reaction mixture of the transesterification is admixed with methanol and then cooled to from 0° to 20° C., particularly advantageously to from 3° to 5° C. In this way, the product is obtained in a particularly readily filterable and washable form. The product which has crystallized out is then isolated by filtration or centrifugation, washed with methanol and dried. A yellow crystalline powder results. If a mixture of the 1-methoxy-2-propyl ester I and the methyl ester II is formed in the transesterification and the compound I is to be prepared in pure form, the mixture can be fractionated by customary methods known to those skilled in the art, for example by recrystallization or chromatography.

The 1-methoxy-2-propyl ester of the formula I or the mixture of the 1-methoxy-2-propyl ester of the formula I and the methyl ester of the formula II prepared by the process of the invention has a high purity. In contrast to the product obtained according to U.S. Pat. No. 5,225,312, virtually no impurities are present according to the high-pressure liquid chromatogram. In addition, the process of the invention gives the transesterification product in a high yield of about 100 percent by weight, based on the weight of the methyl ester of the formula II used, and the space yield is below 5 l/kg. A degree of transesterification of over 50% is easily achieved by the process of the invention.

The invention further provides a process for preparing 1-methoxy-2-propyl 3-(7-diethylamino-2-oxo-2H-chromen-3-yl)-3-oxopropionate of the formula I or mixtures of 1-methoxy-2-propyl 3-(7-diethylamino-2-oxo-2H-chromen-3-yl)-3-oxopropionate of the formula I and alkyl 3-(7-diethylamino-2-oxo-2H-chromen-3-yl)-3-oxopropionate of the formula IV in which R is $(C_1-C_4)$-alkyl,

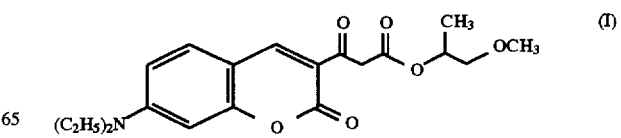

-continued

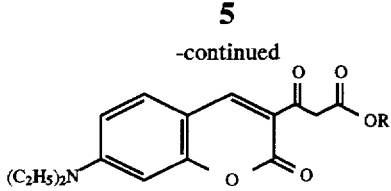

which comprises first transesterifying a dialkyl acetonedicarboxylate of the formula V in which R is $(C_1-C_4)$-alkyl with 1-methoxy-2-propanol of the formula III to give di(1-methoxy-2-propyl) acetonedicarboxylate of the formula VI or a mixture of the ester of the formula VI, the ester of the formula V and the corresponding mixed ester

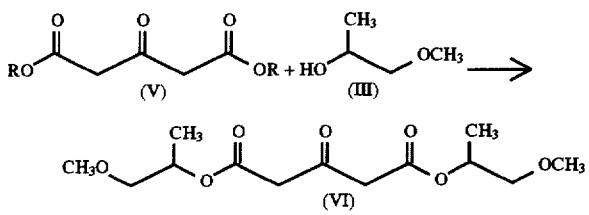

and then reacting the transesterification product with 4-diethylamino-salicylaldehyde of the formula VII.

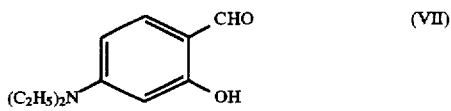

Examples of the alkyl radical R are methyl, ethyl, n-propyl, isopropyl, n-butyl, isobutyl, sec-butyl and tert-butyl. R is preferably methyl or ethyl, particularly preferably methyl. Thus, in the particularly preferred embodiment of this invention dimethyl acetonedicarboxylate is used and 1-methoxy-2-propyl 3-(7-diethylamino-2-oxo-2H-chromen-3-yl)-3-oxopropionate of the formula I or mixtures of 1-methoxy-2-propyl 3-(7-diethylamino-2-oxo-2H-chromen-3-yl)-3-oxopropionate of the formula I and methyl 3-(7-diethylamino-2-oxo-2H-chromen-3-yl)-3-oxopropionate of the formula III are prepared.

The transesterification of the dialkyl acetonedicarboxylate of the formula V occurring in the first stage of the process of the invention can be carried out in a manner similar to known transesterification methods. It is preferably carried out as described in J. Am. Chem. Soc. 73 (1951), 4195 under neutral conditions with the alcohol ROH being distilled off. For this purpose, a mixture of the compound of the formula V and 1-methoxy-2-propanol of the formula III is heated, for example to a temperature of from 90° to 140° C. The degree of conversion can be followed by means of the amount of alcohol ROH disilled off or by gas chromatography and can be varied within wide limits for the purpose of giving optimal use properties of the photoresist dye to be prepared. The ester of the formula VI or the mixture of the ester of the formula VI, the ester of the formula V and the corresponding mixed ester can be isolated as intermediates, for example by distillation, but the transesterification product or the entire reaction mixture of the transesterification reaction can also be used directly in the second stage of the process. If desired, the pure di(1-methoxy-2-propyl) acetonedicarboxylate of the formula VI can be isolated by customary methods, for example by distillation or chromatography, from the reaction mixture from the transesterification carried out in the first stage. The present invention also provides di(1-methoxy-2-propyl) acetonedicarboxylate of the formula VI and also provides for its use for preparing the 1-methoxy-2-propyl ester of the formula I.

The reaction of the transesterification product with 4-diethylaminosalicylaldehyde of the formula VII occurring in the second stage of the process of the invention can be carried out in an inert organic solvent with base catalysis in accordance with the procedure in DE-C-2 704 368. Preferred solvents are ethers, alcohols and partially etherified polyhydric alcohols. Examples which may be mentioned are dialkyl ethers such as dipropyl or dibutyl ether, cyclic ethers such as tetrahydrofuran or dioxane, monoalkyl and dialkyl ethers of ethylene glycol and propylene glycol and of diethylene, oligoethylene, dipropylene and oligopropylene glycols such as ethylene glycol monomethyl or dimethyl ether or propylene glycol monomethyl ether, or alkanols such as methanol, ethanol, n-propanol, isopropanol or n-butanol. A particularly preferred solvent is 1-methoxy-2-propanol. It is also possible to use solvent mixtures, in particular mixtures of the solvents mentioned, and also mixtures of one or more organic solvents with water.

Suitable bases are organic bases such as amines and inorganic bases such as alkali metal and alkaline earth metal hydroxides, alkaline earth metal oxides and the carbonates and hydrogencarbonates of alkali and alkaline earth metals, with examples of these metals being lithium, sodium, potassium, cesium, magnesium, calcium and barium. Preference is given to using organic bases because this rules out the presence in the product of traces of metal which could interfere in the use of the product in photoresists. Particularly preferred bases are secondary amines, for example diethylamine, pyrrolidine, piperidine and morpholine; very particular preference is given to morpholine and piperidine. It is also possible to use mixtures of two or more bases. The amount of base depends on the individual case and can be varied within wide limits depending on the desired course of the reaction. Generally from 0.05 to 2.5 mol of base, preferably from 0.1 to 1 mol of base, particularly preferably from 0.1 to 0.6 mol of base, are used per mol of 4-diethylaminosalicylaldehyde of the formula VII.

The reaction of the transesterification product from the first stage with the 4-diethylaminosalicylaldehyde of the formula VII is carried out in a customary manner. The transesterification product can here be used in the form of the reaction mixture from the first stage, i.e. without any work-up after the transesterification step, in the form of a crude product isolated as an intermediate or not isolated, or in purified form. For example, the transesterification product can be mixed with the aldehyde of the formula VII and the solvent, the mixture can then be brought while stirring to the desired reaction temperature and the base can be added at this temperature all at once or slowly over a relatively long period of time. The reaction mixture is then held at the reaction temperature until the reaction is complete or the desired degree of conversion has been reached. However, the catalytically active base can likewise be added before the reaction temperature is set or during a heating procedure. Likewise, for example, only the transesterification product or only the aldehyde of the formula VII can be initially charged together with the solvent and the other reactant plus the base can subsequently be added at the desired temperature. The reaction is generally carried out at atmospheric pressure between room temperature and the reflux temperature of the solvent or the reaction mixture. However, it can also be carried out at higher temperatures and under pressure, and the temperature can also be altered during the reaction, for example increased once again toward the end to complete the reaction. The second stage of the process of the invention is preferably carried out at from 40° to 90° C., particularly preferably at from 50° to 80° C. The reaction is generally complete after from 0.5 to 6 hours.

In the second stage, the acetonedicarboxylate ester of the formula VI or the mixture of the esters present after the transesterification is advantageously used in a small excess based on the aldehyde of the formula VII. Preference is given to using from 0.8 to 0.95 mol of 4-diethylaminosalicylaldehyde of the formula VII per mol of ester or ester mixture.

The reaction mixture from the second stage can be worked up by a method similar to that described above in the section on the transesterification of II to give I, e.g. by cooling and/or precipitation, if desired in each case after partial evaporation, and centrifugation or filtering off of the 1-methoxy-2-propyl ester of the formula I or the mixture of the ester of the formula I and the ester of the formula IV which has crystallized out. Here too, if desired, the pure ester of the formula I can be isolated from a mixture by customary methods. The work-up can here also be carried out in a preferred and particularly simple manner by cooling in the presence of an additional organic solvent as precipitant, particularly in the presence of methanol which leads to an improved, particularly readily filterable and washable crystalline form. Very particularly preferably, the reaction mixture is admixed hot with methanol and then cooled to from 0° to 20° C., in particular to from 5° to 10° C.

The process of the invention gives, in a technically simple manner, good yields of about 70% of the 1-methoxy-2-propyl ester of the formula I or mixtures of the 1-methoxy-2-propyl ester of the formula I and the alkyl ester of the formula IV having high contents of 1-methoxy-2-propyl ester of over 90%. The products are notable, in particular, for a high purity. The space yield is below 10 l/kg.

EXAMPLES

Comparative Example (in accordance with Example 4 in U.S. Pat. No. 5,225,312)

150 g (0.473 mol) of methyl 3-(7-diethylamino-2-oxo-2H-chromen-3-yl)-3-oxopropionate are initially charged in 1125 g (12.5 mol) of 1-methoxy-2-propanol and admixed with 60 g (0.6 mol) of 98 percent strength sulfuric acid. The mixture is heated to 80° C. and held for 3 hours at this temperature. Volatile constituents are then distilled off at 80° C. with application of a vacuum. After a total of 6 hours at 80° C., the mixture is cooled to 50° C. and admixed with 250 g (2.87 mol) of morpholine to neutralize the sulfuric acid. The dye solution is then poured while stirring vigorously into 2 l of water at 10° C. The product which has crystallized out is filtered off with suction and washed with 1 l of water a little at a time. The product is dried in vacuo.

Yield: 130 g (86.7 percent by weight, based on the weight of the methyl ester used)

According to the high-pressure liquid chromatogram, the product comprises 16.6 percent by area of 1-methoxy-2-propyl 3-(7-diethylamino-2-oxo-2H-chromen-3-yl)-3-oxopropionate and 44.5 percent by area of methyl 3-(7-diethylamino-2-oxo-2H-chromen-3-yl)-3-oxopropionate plus numerous impurities.

Example 1

150 g (0.473 mol) of methyl 3-(7-diethylamino-2-oxo-2H-chromen-3-yl)-3-oxopropionate are initially charged in 280 g (3.11 mol) of 1-methoxy-2-propanol and heated to 110° C. After 2 hours at 110° C., the reaction mixture is cooled to 70° C. and admixed over a period of 2 hours at 60°–70° C. with 280 g of methanol. It is then cooled to 5° C., the product which has crystallized out is filtered off with suction and washed with methanol. The product is dried in vacuo.

Yield: 150.8 g (100.5 percent by weight, based on the weight of the methyl ester used)

According to the high-pressure liquid chromatogram, the product comprises 55.9 percent by area of 1-methoxy-2-propyl 3-(7-diethylamino-2-oxo-2H-chromen-3-yl)-3-oxopropionate and 44.1 percent by area of methyl 3-(7-diethylamino-2-oxo-2H-chromen-3-yl)-3-oxopropionate.

Example 2

A mixture of 34.8 g (0.2 mol) of dimethyl acetonedicarboxylate and 54 g (0.6 mol) of 1-methoxy-2-propanol is heated to an internal temperature of 120°–140° C. At this temperature, 12 ml (about 0.3 mol) of methanol are distilled off via a column (15 cm; Raschig rings). 300 ml of 1-methoxy-2-propanol are added to the resulting mixture and 36.5 g (0.19 mol) of 4-diethylaminosalicylaldehyde are introduced. After stirring for 15 minutes at room temperature, 9.8 g (0.11 mol) of morpholine are added, the mixture is heated to 67°–70° C. over a period of 1 hour and is stirred further for 1 hour at this temperature. It is then cooled to 5°–10° C., the precipitated product is filtered off with suction, washed with methanol and dried.

Yield: 47.9 g

According to the high-pressure liquid chromatogram, the product comprises 92.7 percent by area of 1-methoxy-2-propyl 3-(7-diethylamino-2-oxo-2H-chromen-3-yl)-3-oxopropionate and 6.6 percent by area of methyl 3-(7-diethylamino-2-oxo-2H-chromen-3-yl)-3-oxopropionate.

Example 3

A mixture of 34.8 g (0.2 mol) of dimethyl acetonedicarboxylate and 54 g (0.6 mol) of 1-methoxy-2-propanol is heated to an internal temperature of 120°–140° C. At this temperature, 6 ml (about 0.15 mol) of methanol are distilled off via a column (15 cm; Raschig rings). 300 ml of 1-methoxy-2-propanol are added to the resulting mixture and 36.5 g (0.19 mol) of 4-diethylaminosalicylaldehyde are introduced. After stirring for 15 minutes at room temperature, 9.8 g (0.11 mol) of morpholine are added, the mixture is heated to 67°–70° C. over a period of 1 hour and stirred further for 1 hour at this temperature. It is then diluted with 300 ml of methanol, cooled to 5°–10° C., and the precipitated product is filtered off with suction, washed with methanol and dried.

Yield: 46.9 g

According to the high-pressure liquid chromatogram, the product comprises 63.5 percent by area of 1-methoxy-2-propyl 3-(7-diethylamino-2-oxo-2H-chromen-3-yl)-3-oxopropionate and 35.5 percent by area of methyl 3-(7-diethylamino-2-oxo-2H-chromen-3-yl)-3-oxopropionate.

Example 4

A mixture of 34.8 g (0.2 mol) of dimethyl acetonedicarboxylate and 54 g (0.6 mol) of 1-methoxy-2-propanol is heated to an internal temperature of 120°–140° C. At this temperature, 12 ml (about 0.3 mol) of methanol are distilled off via a column (15 cm; Raschig rings). The resulting mixture is first freed under reduced pressure of excess 1-methoxy-2-propanol and then fractionally distilled under reduced pressure.

$^1$H-NMR spectrum of the di(1-methoxy-2-propyl) acetonedicarboxylate obtained as main component (in $D_6$-DMSO; δ (ppm)):

1.2 (d, 6H, CH$_3$—CH—), 3.3 (s, 6H, CH$_3$—O—), 3.4 (d, 4H, —CH$_2$—O—), 3.7 (s, 4H, —CO—CH$_2$—CO—), 5.0 (m, 2H, O—C$\underline{H}$(CH$_3$)CH$_2$—).

We claim:

1. A process for preparing 1-methoxy-2-propyl 3-(7-diethylamino-2-oxo-2H-chromen-3-yl)-3-oxopropionate of the formula I or mixtures of 1-methoxy-2-propyl 3-(7-diethylamino-2-oxo-2H-chromen-3-yl)-3-oxopropionate of the formula I and methyl 3-(7-diethylamino-2-oxo-2H-chromen-3-yl)-3-oxopropionate of the formula II, which comprises transesterification of methyl 3-(7-diethylamino-2-oxo-2H-chromen-3-yl)-3-oxopropionate of the formula II with 1-methoxy-2-propanol of the formula III,

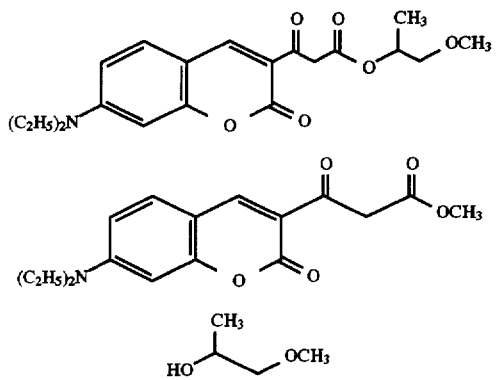

wherein no catalyst is added in the transesterification.

2. The process as claimed in claim 1, wherein the transesterification is carried out at from 80° to 150° C.

3. The process as claimed in claim 1, wherein from 5 to 10 mol of 1-methoxy-2-propanol of the formula III are used per mol of methyl ester of the formula II.

4. The process as claimed in claim 1 wherein methanol is added to the transesterification mixture to isolate the transesterification product.

5. A process for preparing 1-methoxy-2-propyl 3-(7-diethylamino-2-oxo-2H-chromen-3-yl)-3-oxopropionate of the formula I or mixtures of 1-methoxy-2-propyl 3-(7-diethylamino-2-oxo-2H-chromen-3-yl)-3-oxopropionate of the formula I and alkyl 3-(7-diethylamino-2-oxo-2H-chromen-3-yl)-3-oxopropionate of the formula IV in which R is (C$_1$–C$_4$)-alkyl,

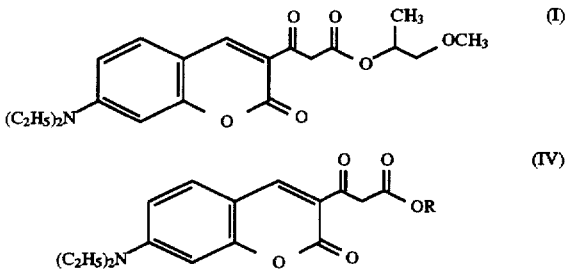

which comprises first transesterifying a dialkyl acetonedicarboxylate of the formula V in which R is (C$_1$–C$_4$)-alkyl with 1-methoxy-2-propanol of the formula III to give di(1-methoxy-2-propyl) acetonedicarboxylate of the formula VI or a mixture of the ester of the formula VI, the ester of the formula V and the corresponding mixed ester

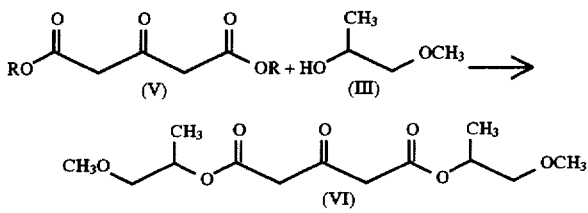

and then reacting the transesterification product first obtained with 4-diethylamino-salicylaldehyde of the formula VII.

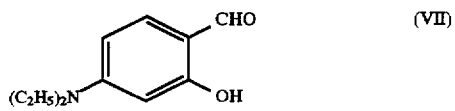

6. The process as claimed in claim 5, wherein R is methyl or ethyl.

7. The process as claimed in claim 5, wherein the transesterification product first obtained is not isolated as an intermediate.

8. The process as claimed in claim 5, wherein the reaction of the transesterification product first obtained with the aldehyde of the formula VII is carried out with base catalysis.

9. The process as claimed in claim 5, wherein, after reacting the transesterification product first obtained with 4-diethylaminosalicylaldehyde of the formula VII to obtain a reaction mixture containing the product of formula I, methanol is added to the reaction mixture to isolate said product.

10. Di(1-methoxy-2-propyl) acetonedicarboxylate.

11. The process as claimed in claim 1, wherein the transesterification is carried out at from 90° to 130° C.

12. The process as claimed in claim 1, wherein the transesterification is carried out at from 100° to 120° C.

13. The process as claimed in claim 3, wherein the molar amount of 1-methoxy-2-propanol is 6 to 8 mol per mol of methyl ester of the formula II.

14. A process for preparing 1-methoxy-2-propyl-3-(7-diethylamino-2-oxo-2H-chromen-3-yl)-3-oxopropionate or mixtures thereof with methyl 3-(7-diethylamino-2-oxo-2H-chromen-3-yl)-3-oxopropionate, which comprises:

transesterifying methyl 3- (7-diethylamino-2-oxo-2H-chromen-3-yl)-3-oxopropionate with 1-methoxy-2-propanol under conditions which are neutral except with respect to the basicity of the diethylamino group of said methyl 3-(7-diethylamino-2-oxo-2H-chromen-3-yl)-3-oxopropionate or said 1-methoxy-2-propyl-3-(7-diethylamino-2-oxo-2H-chromen-3-yl)-3-oxopropionate.

15. The process as claimed in claim 8, wherein said reaction is carried out in the presence of a secondary amine as a basic catalyst.

16. The process as claimed in claim 15, wherein said secondary amine is morpholine or piperidine.

* * * * *